US012478171B2

(12) United States Patent
Luchesi

(10) Patent No.: US 12,478,171 B2
(45) Date of Patent: Nov. 25, 2025

(54) THERAPEUTIC FIDGET OR MEMORY ITEM

(71) Applicant: Ava James Luchesi, Avon Lake, OH (US)

(72) Inventor: Ava James Luchesi, Avon Lake, OH (US)

( * ) Notice: Subject to any disclaimer, the term of this patent is extended or adjusted under 35 U.S.C. 154(b) by 264 days.

(21) Appl. No.: 18/047,671

(22) Filed: Oct. 19, 2022

(65) Prior Publication Data

US 2023/0263289 A1 Aug. 24, 2023

Related U.S. Application Data

(60) Provisional application No. 63/312,877, filed on Feb. 23, 2022.

(51) Int. Cl.

| | |
|---|---|
| ***A45F 5/02*** | (2006.01) |
| ***A45F 5/00*** | (2006.01) |
| ***A47G 1/16*** | (2006.01) |
| ***A47G 9/02*** | (2006.01) |
| ***A61M 21/00*** | (2006.01) |
| ***A61M 21/02*** | (2006.01) |

(52) U.S. Cl.

CPC .............. *A45F 5/02* (2013.01); *A47G 1/1653* (2013.01); *A47G 9/0223* (2013.01); *A61M 21/02* (2013.01); *A45F 5/155* (2025.01); *A61M 2021/0022* (2013.01); *A61M 2021/0044* (2013.01)

(58) Field of Classification Search

CPC ............ A47G 9/0223; A47G 2009/004; A47G 1/1653; A41D 11/00; A41D 2200/20; A41D 23/00; A41D 2400/32; A41D 3/08; A41D 31/02; A61M 21/02; A61M 2021/0022; A61M 2021/0044; A45F 2200/055

See application file for complete search history.

(56) References Cited

U.S. PATENT DOCUMENTS

| | | | | |
|---|---|---|---|---|
| 5,898,962 | A * | 5/1999 | McNeal | A47G 9/1045 5/639 |
| 7,107,638 | B2 * | 9/2006 | Wilson | A47G 9/0207 5/923 |
| 10,157,557 | B1 * | 12/2018 | Martin | G09F 23/00 |
| D898,454 | S * | 10/2020 | Coleman | D6/603 |

OTHER PUBLICATIONS

"Fidget Quilts for ALZHEIMERS| Key Biscayne| Linda Manla." YouTube, YouTube, Jun. 30, 2017 https://www.youtube.com/watch?v=WyVs3slku4Y (Year: 2017).*

* cited by examiner

*Primary Examiner* — David R Hare
*Assistant Examiner* — Deborah Talitha Gedeon
(74) *Attorney, Agent, or Firm* — Kenneth S. Luchesi

(57) ABSTRACT

Therapeutic blankets and therapeutic clothing, such as shirts, jackets, and vests, are provided. In embodiments of the present disclosure, the therapeutic blankets and therapeutic clothing include at least one memory item and at least one fidget item. The at least one memory item and the at least one fidget item are removably attached to the therapeutic blankets and the therapeutic clothing.

2 Claims, 2 Drawing Sheets

THERAPEUTIC FIDGET OR MEMORY ITEM

CROSS-REFERENCE TO RELATED APPLICATION

This application claims priority to U.S. Provisional Application No. 63/312,877, filed Feb. 23, 2022, which is incorporated herein by reference in its entirety.

TECHNICAL FIELD

This disclosure relates to therapeutic items, such as blankets, shirts, vests, or jackets, and more particularly to a blanket or clothing item that includes removable and replaceable fidget items, memory items, and related accessories.

BACKGROUND

Functional clothing refers to garments that provide functionality aside from aesthetics and basic protection of the wearer. Examples of functional clothing include sports-functional clothing (e.g., garments that provide moisture wicking) and medical-functioning clothing (e.g., surgical clothing). Functional clothing also includes therapeutic clothing that helps to cure, treat, or improve a person's condition.

BRIEF DESCRIPTION OF THE DRAWINGS

The present disclosure will be understood more fully from the detailed description given below and from the accompanying drawings of various embodiments of the present disclosure, which, however, should not be taken to limit the present disclosure to the specific embodiments, but are for explanation and understanding only.

DETAILED DESCRIPTION

Figure 2:
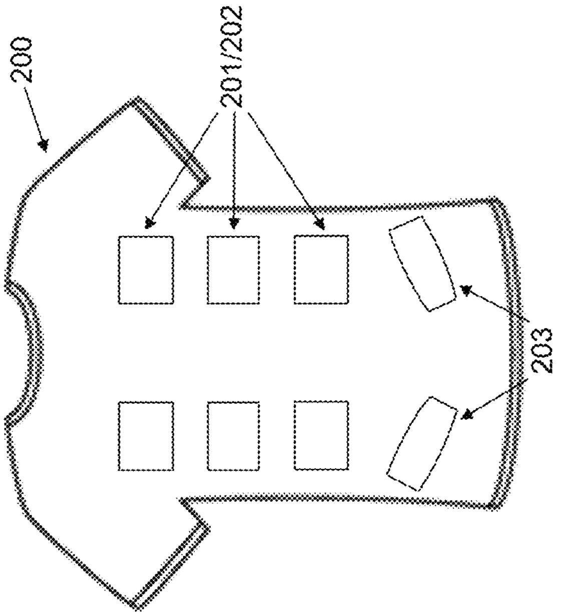
FIG. 2 illustrates a shirt or jacket, in accordance with some embodiments of the disclosure.

The following disclosure provides many different embodiments, or examples, for implementing different features of the provided subject matter. Specific examples of components and arrangements are described below to simplify the present disclosure. These are, of course, merely examples and are not intended to be limiting.

The average attention span for a healthy adult is just under 20 minutes. But even then, many people resort to fidgeting to help them pay better attention. In fact, research has found that just a small amount of movement, like fidgeting with hands, increases dopamine and norepinephrine—neurotransmitters which aid attention and focus. For individuals with Alzheimer's or dementia, however, staying focused is inherently a much greater challenge. Alzheimer's also significantly affects an individual's memory. The disease affects the hippocampus, which is a portion of the temporal lobe that plays a large role in both learning and memory.

As the disease progresses, more complicated movements become difficult or impossible, which can cause anxiety or agitation. When an individual with Alzheimer's or dementia is stressed or anxious, it is often evident in their hands. They tend to pull at their clothes or bedding, rub their skin, wring their hands and twist their fingers when they're upset or agitated. These behaviors are how they deal with their discomfort. For these individuals, having something to soothe, stroke or fidget with may ease that anxiety and agitation. According to experts, sensory therapy, including the use of "fidget toys," can safely soothe these individuals by keeping their hands busy in a productive and positive way.

Additional research has explored how people with dementia experience changes to their visual cortex, including narrowed peripheral vision, difficulty with color and pattern contrast, problems with depth of field, etc. For these reasons, fidget items for these individuals should be designed accordingly. For example, items with interesting and varying textures and weight can capture the attention of individuals with Alzheimer's or dementia, and help to ease their anxiety and nervousness. Additionally, beyond the use of various textures, etc. to stimulate the sensory system, fidget items may also incorporate activities that encourage the individual to move their hands, such as by opening and closing zippers, attaching and detaching Velcro, moving beads, etc.

In addition, people with neurodegenerative diseases often have a narrowed peripheral vision, and in advanced cases, the individual's field of vision may reduce to just 12 inches around. Therefore, fidget or memory items that are presented to such individuals should generally be small, so the individual is able to see and manage the item. People with Alzheimer's or dementia may also struggle with differences in contrast and may be bothered by white, opaque, shiny or reflective items. They may also struggle with depth perception. For these reasons, it is important for fidget or memory items to be relatively simple, and to be brightly colored with obvious contrast.

Fidget items that provide sensory and cognitive stimulation for individuals with Alzheimer's or dementia are usually items that children enjoy as well. Therefore, such items also offer an opportunity to encourage interaction between children and elders.

There is a need for therapeutic items, such as blankets or clothing, that are completely customizable with various fidget and/or memory items, that keep all of these items in one place, connected to one another, so as not to get lost and to provide extended stimulation for the user, and that allows the items to be removed and replaced, to provide the ability to stimulate in different ways, invoke memories of different people or places, and avoid boredom from repetitive use of the same items. Although particularly useful for patients with Alzheimer's or dementia, such therapeutic items may be useful for many other individuals suffering from a variety of illnesses, and who need an item to soothe their mind and/or provide a distraction for their hands and body.

Embodiments of this disclosure address one or more of these objectives. As detailed below, embodiments of this disclosure relate to therapeutic items that may be used to soothe or calm a patient that is restless, or to assist with memories, or to provide therapeutic comfort in any way. As described below, the therapeutic item may be a blanket, a clothing item such as a shirt, vest, jacket, or pants, or any other therapeutic item that may be configured and arranged as described herein. The therapeutic item may include fidget items, memory items, a combination of memory and fidget items, and other decorative items or embroidery.

Fidget items are intended to provide something for the user to engage with their hands. Fidget items may include beads, zippers, buttons, buckles, locks, braided fabric, hook and loop strips (such as Velcro® strips), monkey noodles, squishies, wacky tracks, stress balls, marbles in mesh, latches, fidget cubes, fidget pads, pea poppers, pop-its, or any other similar item that provides physical or visual stimulation to the user.

Memory items may be photographs or drawings of loved ones, photographs or drawings of favorite locations or activities, gifts or heirlooms from a loved one or from a special vacation, or any similar item that assists in helping the user remember a particular person, place, or activity. The memory item may also be a sleeve or other pocket into which a photograph or drawing is inserted. In one embodiment, the sleeve or pocket may include a flap that either opens, or is removed to reveal the photograph or drawing. In the embodiment where the memory item is a photograph or drawing, the item may be inserted into a sleeve or pocket as described above, or it may be directly attached to the blanket, such as by clipping, gluing, sewing, or any other suitable means. In the embodiment where the memory item is a gift or heirloom or other item that is used to remember a particular person, the item may either be directly attached to the blanket, or in other embodiments it may be inserted into a pocket, which pocket may be removably attached to the blanket as described below.

The blanket may include only fidget items, it may include only memory items, or it may include a combination of both. The fidget items or memory items may be permanently attached to the blanket, for example by being sewn in. Alternatively and preferably, they may be removable and replaceable. This allows a family member or caregiver to change the fidget or memory items on a daily or weekly basis, or however frequently is necessary or desired. In areas of the blanket where no fidget item or memory item is attached, the blanket may also include embroidery, such as flowers or animals, or may include initials or monograms, or any other decorative item or feature. In this way the blanket is completely customizable.

In embodiments where the fidget items or memory items are removable, the items may be connected in a variety of ways. The blanket may include permanent attachment points, and the fidget items or memory items may be removably attached to those permanent attachment points by hook and loop (such as Velcro®), by buttons, by zippers, by clips, by carabine, by adhesive, or by any other well-known method of attaching two items in a removable way.

Figure 1:
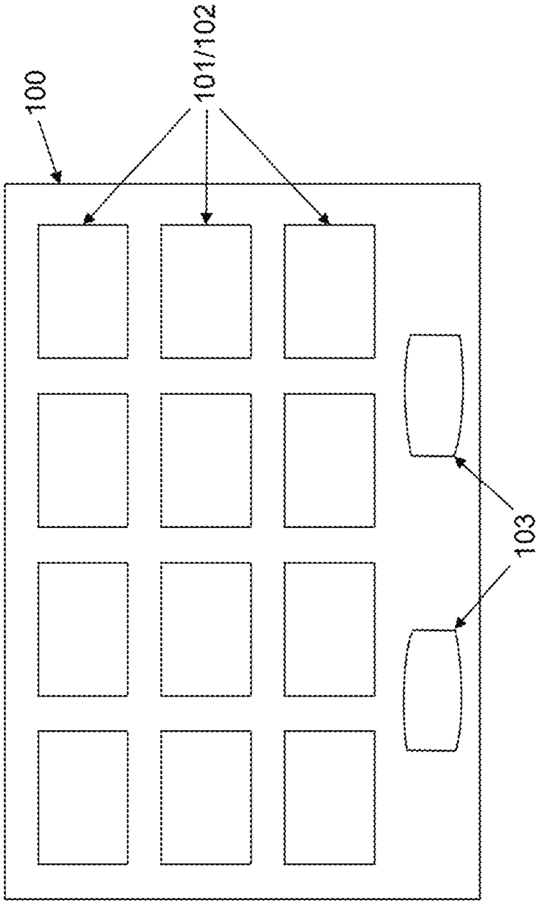
FIG. 1 illustrates a blanket, in accordance with some embodiments of the disclosure.

The fidget items or memory items may be arranged on the blanket [100] in a variety of ways. FIG. 1 shows one example of arranging the fidget items [101] and/or memory items [102] in a grid pattern. The blanket may include any number of fidget items and/or memory items as determined by the user, his or her family member, or other caregiver, and the fidget items and/or blanket items may be arranged on the blanket in whatever configuration the user desires. As just one illustrative example, if an individual has lost use of one arm, the fidget items and/or memory items may be primarily arranged on one side of the blanket. The blanket may also include pouches [103] that are zippered or otherwise sewn that can act as pockets for the user to put his or her hands in.

Although the disclosure has been described primarily with respect to a blanket, alternative embodiments of the disclosure incorporate the above-described fidget items and/or memory items on an article of clothing. Individuals suffering with Alzheimer's or dementia are known to often pick up items, take them somewhere else, and leave them there. By incorporating the present disclosure into an article of clothing, it will always be present on the individual while they are wearing the item, thus making it less likely that the individual will misplace the item or be without it. This is especially true for individuals with more progressed disease as they would be unlikely to undress themselves, and thus remove the item. In accordance with the present disclosure, the article of clothing will be completely customizable as described above.

Figure 3:
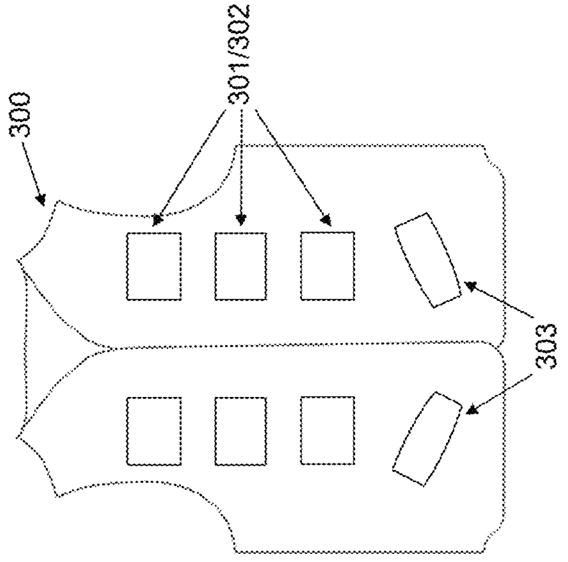
FIG. 3 illustrates a vest, in accordance with some embodiments of the disclosure.

One example of this embodiment, shown in FIG. 2, is to incorporate the fidget items [201] and/or memory items [202] on a shirt [200]. Similar to the blanket, the shirt may also incorporate pockets for the individual's hands [203]. Alternatively, as shown in FIG. 3, the fidget items [301] and/or memory items [302], and pockets [303], may be incorporated into a vest [300]. As alternative options, the fidget items and/or memory items may also be incorporated into a jacket, or pants, or any other item that can be worn and that incorporates the features described herein.

The foregoing description is merely illustrative in nature and is not intended to limit the embodiments of the subject matter or the application and uses of such embodiments. Furthermore, there is no intention to be bound by any expressed or implied theory presented in the technical field, background, or the detailed description. As used herein, the word "exemplary" means "serving as an example, instance, or illustration." Any implementation described herein as exemplary is not necessarily to be construed as preferred or advantageous over other implementations, and the exemplary embodiments described herein are not intended to limit the scope or applicability of the subject matter in any way.

What is claimed:

1. A therapeutic blanket comprising:

a plurality of memory items; and a plurality of fidget items;

wherein the plurality of memory items and the plurality of fidget items are removably attached and symmetrically arranged in a grid pattern to a top surface of the therapeutic blanket using a plurality of attachment mechanisms, such that at least one memory item is configured to be replaced by a different memory item using the same attachment mechanism, and the at least one fidget item can be replaced by a different fidget item using the same attachment mechanism, wherein at least one memory item further includes a photograph or a drawing, wherein the photograph or drawing is removably attached to a permanent attachment point on the therapeutic blanket by a hook and loop fastener, wherein the blanket includes a transparent sleeve into which the photograph or drawing is removably inserted, wherein the transparent sleeve includes a non-transparent cover that can be removed or opened to reveal the photograph or drawing, wherein the blanket further includes pouches that are zippered to the top surface of the therapeutic blanket below the grid pattern of the plurality of memory and/or fidget items and the pouches being configured for a user to put a hand within, wherein the fidget item is removably attached to a permanent attachment point on the therapeutic blanket by carabiner, wherein the blanket further has embroidery selected from the group consisting of flowers, animals, and initial monograms.

2. The therapeutic blanket of claim 1, wherein the fidget item is selected from the group comprising beads, zippers, buttons, buckles, locks, and braided fabric.

* * * * *